United States Patent
Ahmad et al.

(10) Patent No.: US 11,098,095 B1
(45) Date of Patent: Aug. 24, 2021

(54) METHODS OF INHIBITING MMP-9

(71) Applicant: DASMAN DIABETES INSTITUTE, Dasman (KW)

(72) Inventors: Rasheed Ahmad, Dasman (KW); Fahd Al Mulla, Dasman (KW)

(73) Assignee: DASMAN DIABETES INSTITUTE, Dasman (KW)

( * ) Notice: Subject to any disclaimer, the term of this patent is extended or adjusted under 35 U.S.C. 154(b) by 0 days.

(21) Appl. No.: 17/073,620

(22) Filed: Oct. 19, 2020

(51) Int. Cl.
*A61K 31/497* (2006.01)
*C07K 14/47* (2006.01)
*C07D 239/00* (2006.01)
*A61K 38/00* (2006.01)
*A61K 31/498* (2006.01)

(52) U.S. Cl.
CPC ........ *C07K 14/4703* (2013.01); *C07D 239/00* (2013.01); *A61K 31/497* (2013.01); *A61K 31/498* (2013.01); *A61K 38/00* (2013.01)

(58) Field of Classification Search
CPC .. A61K 31/497; A61K 31/498; A61K 31/277; C07D 403/12; C07D 487/14
See application file for complete search history.

(56) References Cited

U.S. PATENT DOCUMENTS

| | | |
|---|---|---|
| 2006/0235034 A1 | 10/2006 | Neamati |
| 2009/0093489 A1 | 4/2009 | Neamati et al. |
| 2011/0263525 A1 | 10/2011 | Turkson |
| 2012/0157500 A1 | 6/2012 | Tao |

FOREIGN PATENT DOCUMENTS

| | | |
|---|---|---|
| KR | 20140079182 A | 6/2014 |
| WO | 2018167283 A1 | 9/2018 |

OTHER PUBLICATIONS

Lu et al., Up-regulation of hypoxia-inducible factor antisense as a novel approach to treat ovarian cancer, Theranostics, vol. 10, Issue 15, pp. 6959-6976 (May 2020).*
Li et al., Synergistic inhibition of GP130 and ERK signaling blocks chemoresistant bladder cancer cell growth, Cellular Signaling, 63, 10 pages (Jul. 2019).*
He et al., The role of interleukin-6/interleukin-6 receptor signaling in the mechanical stress-induced extracellular matrix remodeling of bladder smooth muscle, Archives of Biochemistry and Biophysics, 8 pages (Nov. 2020).*
Ju et al., IL-6 Regulates Extracellular Matrix Remodeling Associated with Aortic Dilation in a Fibrillin-1 Hypomorphic mgR/mgR Mouse Model of Severe Marfan Syndrome, Journal of the American Heart Association, 13 pages (2014).*
Oshima, T. et al., "Combination effects of SC144 and cytotoxic anticancer agents," Anticancer Drugs, 20(5) pp. 312-320, Jun. 2009.
Xu, S. et al., "Discovery of a Novel Orally Active Small-Molecule gp130 Inhibitor for the Treatment of Ovarian Cancer," Mol. Cancer Therapeutics, 12(6): pp. 937-949, Mar. 27, 2013.
Xu, S. et al., "gp130: a promising drug target for cancer therapy," Expert Opinion on Therapeutic Targets, 17(11) pp. 1303-1328, Oct. 7, 2013.
Tripsianis, G. et al., "Coexpression of IL-6 and TNF-α: prognostic significance on breast cancer outcome," Neoplasma, 61(2): pp. 205-212, 2014.
Masjedi, A. et al., "The significant role of interleukin-6 and its signaling pathway in the immunopathogenesis and treatment of breast cancer," Biomedicine & Pharmacotherapy, 108: pp. 1415-1424, Dec. 2018.

* cited by examiner

*Primary Examiner* — Deepak R Rao
(74) *Attorney, Agent, or Firm* — Nath, Goldberg & Meyer; Richard C. Litman

(57) ABSTRACT

Methods of inhibiting MMP-9 are provided. The methods of inhibiting MMP-9 include methods of inhibiting IL-6/TNF-α crosstalk mediated expression and/or secretion of MMP-9. The inhibition of the IL-6/TNF-α crosstalk pathway may be accomplished using an IL-6 signaling inhibitor, such as AG490 or SC-144. The methods may also include the treatment of dieses through the inhibition of IL-6/TNF-α crosstalk mediated production of MMP-9. In an embodiment the methods may include preventing the progression of cancer or cardiovascular disease through the inhibition of the IL-6/TNF-α crosstalk pathway.

7 Claims, 2 Drawing Sheets

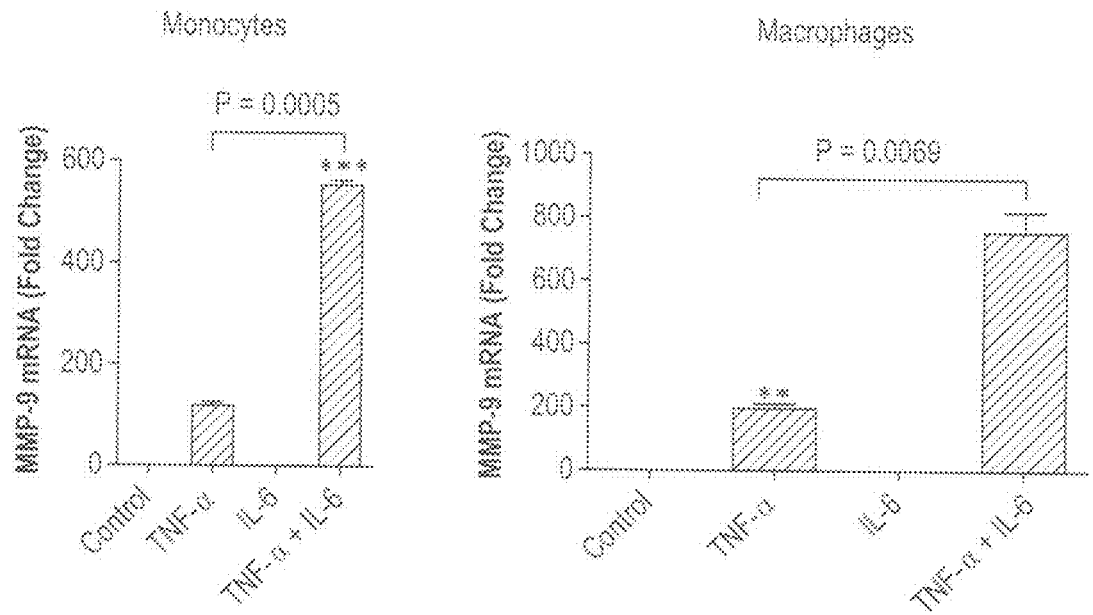
FIG. 1A  FIG. 1B
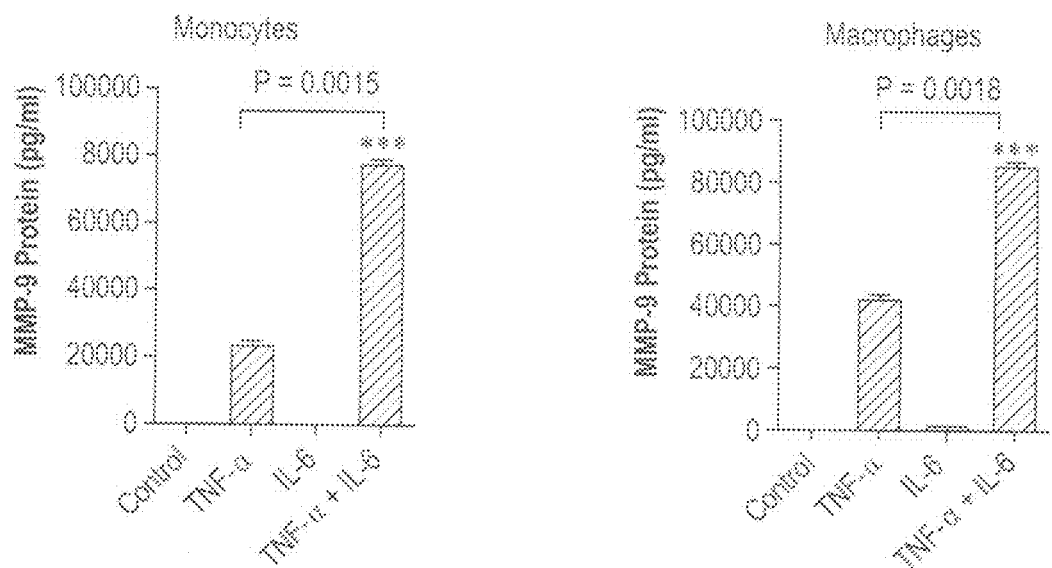
FIG. 2A  FIG. 2B

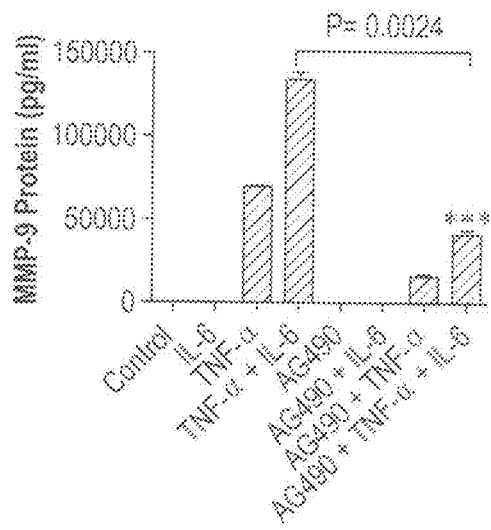
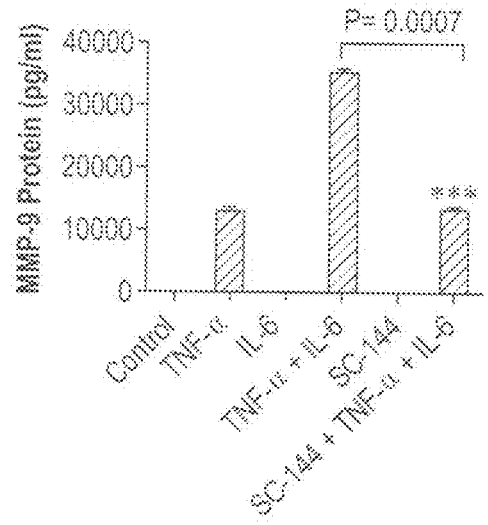
FIG. 3A    FIG. 3B
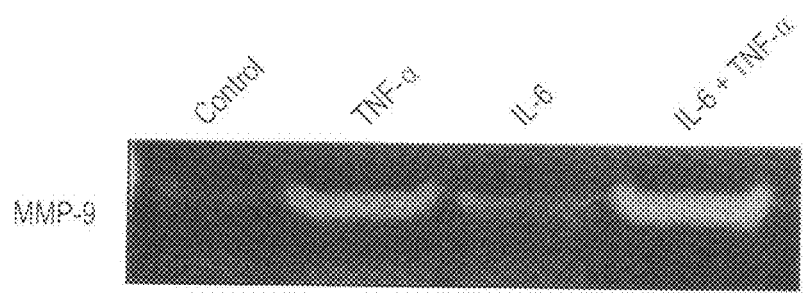
FIG. 4

METHODS OF INHIBITING MMP-9

BACKGROUND

1. Field

The disclosure of the present patent application relates to methods of inhibiting matrix metalloproteinase 9 and particularly to methods of inhibiting MMP-9 by blocking interleukin-6 (IL-6) and tumor necrosis factor alpha (TNF-α) crosstalk pathway mediated MMP-9 expression and secretion.

2. Description of the Related Art

In general matrix metalloproteinases (MMPs) in general and MMP9 in particular are understood to encode proteins that are secreted front the cell and play critical roles in the breakdown of extracellular matrix, in healthy subjects, these proteins are involved in embryonic development, reproduction, angiogenesis, bone development, wound healing, eel migration, and learning and memory. In the pathological context, MMP-9 is understood to be involved in arthritis, cardiovascular disease, and advanced stage cancer development.

MMP-9 understood to play a role in a number of diseases, including particularly in the development of advanced stage cancers. Specifically. MMP-9's role in extracellular matrix remodeling and angiogenesis, paired with observations of increased expression of MMM expression in advanced stage cancers, is thought to suggest a possible, role in facilitating tumor progression, including invasion, metastasis, growth, and angiogenesis, increased MMP-9 expression levels have also been observed in association with progression of idiopathic atrial fibrillation and development of aortic aneurysms.

Thus, control of MMP-9 expression has been of interest in pharmaceutical development. However, early results in developing MMPIs for the treatment of earners have been decidedly mixed, further, the pre-transcriptional and post-transcriptional regulation of MMPs k still only partially understood. Thus, a better understanding of the regulation of MMP expression may identify further new promising pharmaceutical targets.

Thus, methods of inhibiting MMP-9 solving the aforementioned problems are desired.

SUMMARY

The methods of Inhibiting MMP-9 include methods of inhibiting IL-6/TNF-α crosstalk mediated production of MMP-9. The inhibition of the IL-6/TNF-α crosstalk pathway may be accomplished using an IL-6 signaling inhibitor, such as AG490 or SC-144. The methods may also include the treatment of diseases through the inhibition of IL-6/TNF-α crosstalk mediated production of MMP-9.

In an embodiment, the methods may include treatment of diseases such as cancers and cardiovascular diseases in a subject in need thereof. In an embodiment the methods of treatment of diseases such as cancers and cardiovascular diseases may include administration an effective dose of an IL-6 signaling inhibitor to a subject in need thereof whereby the effective dose of the IL-6 signaling inhibitor is a sufficient dose to disrupt fee IL-6/TNF-α crosstalk pathway, thereby inhibiting IL-6/TNF-α mediated MMP-9 expression or secretion and thereby alleviating a symptom or preventing progression of the disease. In an embodiment, the IL-6 signaling inhibitor may include one or more of AG490 and SC-144.

These and other features of the present subject matter will become readily apparent upon further review of the following specification.

BRIEF DESCRIPTION OF THE DRAWINGS

FIG. 1A depicts MMP-9 mRNA expression in monocytes stimulated with TNF-α, IL-6, or TNF-α and IL-6

FIG. 1B depicts MMP-9 mRNA expression in macrophages stimulated with TNF-α, IL-6, or TNF-α and IL-6.

FIG. 2A depicts MMP-9 protein secretion from monocytes stimulated with TNF-α, IL-6, or TNF-α and IL-6

FIG. 2B depicts MMP-9 protein secretion horn macrophages stimulated with TNF-α, IL-6, or TNF-α and IL-6.

FIG. 3A depicts inhibiting the IL-6/TNF-α crosstalk pathway's stimulatory effect on MMP-9 protein secretion by administering AG490.

FIG. 38 depicts inhibiting the IL-6/TNF-α crosstalk pathway's stimulatory effect on MMP-9 protein secretion by administering SC-144.

FIG. 4 depicts proteolytic activity of secreted MMP-9 front monocytes stimulated with TNF-α, IL-6, or TNF-α and IL-6.

Similar reference characters denote corresponding features consistently throughout the attached drawings

DETAILED DESCRIPTION OF THE PREFERRED EMBODIMENTS

The methods of inhibiting MMP-9 include methods of inhibiting IL-6/TNF-α crosstalk mediated production of MMP-9. The inhibition of the IL-6/TNF-α crosstalk, pathway may be accomplished using an IL-6 signaling Inhibitor, such as AG490 or SC-144. The methods may also include the treatment of diseases through the inhibition of IL-6/TNF-α crosstalk mediated production of MMP-9.

As used herein, the term "about" may indicate that a value includes the standard deviation of error for the device or method being employed to determine the value.

As used herein, the term "or" may mean "and/or" unless explicitly indicated to refer to alternatives only or the alternatives are mutually exclusive, although the disclosure supports a definition that refers to only alternatives and "and/or".

As used herein, the term "nucleic acid" means a molecule (having one or more strands) of DNA. RNA or a derivative or analog thereof, comprising a nucleobase. A nucleobase includes, for example, a naturally occurring purine or pyrimidine base found in DNA (e.g., an adenine "A," guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, the term "mRNA" is used according to its ordinary and plain meaning and refers to a messenger RNA molecule typically understood to convey genetic information copied from DNA to the ribosome, where the mRNA sequence is translated to produce a protein from individual amino acids. The term wifi be used to refer to the single-stranded RNA molecule processed from a precursor.

As used herein, "PCR" is any method involving the amplification of a nucleotide sequence based upon complementary primer binding to a target sequence.

As used herein, "RT-PCR" is any method involving the amplification of an RNA sequence using a reverse transcriptase to produce a cDNA sequence, followed by amplification of a nucleotide sequence based upon complementary primer binding to a target sequence.

As used herein, "signal transduction" refers to a process by which a chemical or physical signal is transmitted through a ceil as a series of molecular events (e.g. protein phosphorylation) resulting in a cellular response (e.g. a change in gene expression).

As used herein, "crosstalk" refers to instances wherein components of one or more signal transduction pathways affects another signal transduction pathway.

As used herein, "subject" means a mammal such as a human being.

The inventors have determined that IL-6 and TNF-α both play a roll in the signal transduction pathways that regulate MMP-9 expression. Specifically, the inventors have determined that there Is crosstalk between the roles of IL-6 and TNF-α in the expression and secretion of MMP-9, as exposure to TNF-α increases monocyte and macrophage MMP-9 mRNA expression and protein secretion, but exposure to both TNF-α and IL-6 significantly increases MMP-9 mRNA expression and protein secretion. Further, the inventors have demonstrated that IL-6 inhibitors AG490 and SC-144 suppress the crosstalk effect of IL-6 on TNF-α's enhancement of MMP-9 expression and secretion. Thus, methods of inhibiting MMP-9 expression and/or secretion comprising administering a sufficient amount of one or more IL-6 inhibitors to interfere with the IL-6/TNF-α crosstalk pathway are contemplated herein.

In an embodiment, the methods may include treatment of diseases such as cancers and cardiovascular diseases in a subject in need thereof in an embodiment the methods of treatment of diseases such as cancers and cardiovascular diseases may include administration an effective dose of an IL-6 signaling inhibitor to a subject in need thereof, whereby the effective dose of the it signaling inhibitor is a sufficient dose to disrupt the IL-6/TNF-α crosstalk pathway, thereby inhibiting IL-6/TNF-α mediated MMP-9 expression or secretion, and thereby alleviating a symptom or preventing progression of the disease. In an embodiment the IL-6 signaling inhibitor may include one or more of AG490 and SC-144.

In an embodiment, the methods may include treatment of a cancer to prevent the progression of the cancer. In a further embodiment, the methods may include treatment of s cancer to prevent, the cancer from metastasizing.

In some embodiments, the methods for inhibiting MMP-9 comprise introducing into or providing a subject, tissue, or cell an effective amount of an IL-6 inhibitor.

In certain methods of inhibiting MMP-9, there h a further step of administering & selected IL-6 inhibitor to a cell, tissue, organ, or organism (collectively "biological matter") in need of treatment related to modulation of the inhibition of the IL-6/TNF-α crosstalk pathway or in need of the physiological or biological results discussed herein. Consequently, in some methods there is a step of identifying a subject in need of treatment that can be provided by the IL-6 inhibitors. It is contemplated that an effective amount of an IL-6 inhibitor can be ad man stereo to an identified subject susceptible to such treatment in some embodiments, in particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, or a decrease in a symptom. For example, with respect to cancer, it is contemplated that a therapeutic benefit can be inhibition of the formation of metastasis, inhibition of tumor progression, inhibition of invasion, inhibition of tumor growth, inhibition of MMP-9 expression and/or MMP-9 secretion by turner cells, inhibition of IL-6/TNF-α crosstalk, or a combination thereof.

Furthermore, it is contemplates that the methods for inhibiting MMP-9 may be provided as part of a therapy to a subject, in conjunction with traditional therapies or preventative agents. Moreover, it is contemplated that any method discussed in the context of therapy may be applied as a preventative measure, particularly in a subject identified to be potentially in need of the therapy or at risk of the condition or disease for which a therapy Is needed.

SC-144 is a quinoxalinhydrazide derivative, which operates as an orally-active small molecule gp130 Inhibitor. SC-144 binds gp130 (a transmembrane subunit of an IL-6 receptor), induces gp130 phosphorylation and deglycosylation, abrogates Stat3 phosphorylation and nuclear translocation, and inhibits expression of downstream target genes. Thus, SC-144 is a potent inhibitor of IL-6 signaling (by interfering with the IL-6 cell surface receptor). SC-144 comprises a molecule having the formula:

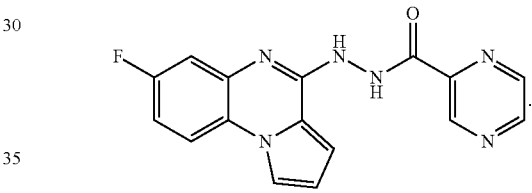

AG490 is a tyrphostin tyrosine kinase inhibitor that induces downregulation of gp130, and thereby prevents IL-6 signaling. Thus, AG490 is a potent inhibitor of IL-6 signaling (by downregulating the expression of the IL-6 ceil surface receptor). AG490 comprises molecule having the formula:

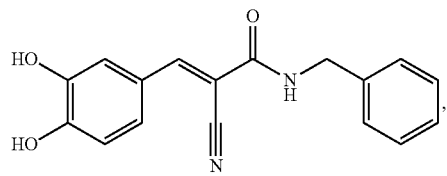 [SMILES: N#C/C(=C\c1ccc(O)c(O)c1)C(=O)NCc1ccccc1]

The following examples illustrate the present teachings

Example 1

Inhibition of Gp130 or JAK2 Abrogated TNF-α/IL-6 Induced MMP9 Expression in Monocytic Cells Monocytes (THP-1 cells and macrophages were cultured in 12-well plates (Costar, Corning Incorporated, Corning, N.Y., USA) at a cell density of $1/10^6$ cells/well. Cells were pre-incubated with gp130 inhibitor (SC-144, 1.5 µM) or JAK2 inhibitor (AG-490, 30 µM) for 1 hour and then stimulated with IL-6 or TNF-α or IL-6/TNF-α for 24 hr at 37° C. (with humidity) in 5% $CO_2$. Control cells were incubated with culture media only. Culture media and cells were harvested and MMP9 mRNA and protein expression levels were assessed by real-time PCR (RT-PCR) and ELISA.

Total RNA was extracted using RNeasy Mini Kit (Qiagen, Valencia, Calif.; USA). The cDNA was synthesized using 1 μg of total RNA using a high capacity cDNA reverse transcription hit (Applied Biosystems, Foster City, Calif., USA). For RT-PCR, cDNA template (50 ng) was amplified using inventoried TaqMan Gene Expression Assay products (MMP-9; Hs00234579_m1; GAPDH; Bs0392909_g1; containing two gene-specific printers and one TaqMan MGB probe (6-FAM dye-labeled) with a TaqMan Gene Expression Master Mix (Applied Biosystems, Foster City, Calif., USA) and a 7500 Fast Real-Time PCR System (Applied Biosystems, Foster City, Calif., USA). The mRNA levels were normalized against GAPDH mRNA and MMP-9 mRNA expression relative to control was calculated using the $2^{-\Delta\Delta Ct}$-method. Relative mRNA expression is shown as told expression over average of control gene expression. MMP-9 gene expression level in control treatment was taken as 1 and the data were presented as mean±SEM values. The results were analyzed statistically and $P<0.05$ was considered significant. The results of these experiments are presents in FIGS. 1A and 1B, illustrating an increase in MMP-9 mRNA expression in response to TNF-α and a significantly larger increase in MMP-9 mRNA expression in response to TNF-α and IL-6, in both monocytes and macrophages.

MMP-9 secreted protein in the supernatants of monocytes and macrophages stimulated with IL-6, TNF-α, or IL-6 and TNF-α was quantified using sandwich ELISA following the manufacturers instructions (SMP900, R&D systems, Minneapolis, USA). The results of this experiment are presented in FIGS. 2A-2B. As illustrated in FIGS. 2A-2B. MMP-9 protein secretion levels are increased in response to stimulation with TNF-α alone and are minimally effected by stimulation with IL-6 alone; however, stimulation with both TNF-α and IL-6 triggers a robust crosstalk effect that significantly Increases the secretion of MMP-9 by monocytes and macrophages when compared to the secretion by monocytes or macrophages stimulated with TNF-α alone. As illustrated in FIGS. 3A-3B, this robust cross-talk effect of IL-6 and TNF-α stimulation on the secretion of MMP-9 by monocytes may be extinguished by administration of either a JAK2 inhibitor AG-490, See FIG. 3A) or a gp130 inhibitor (SC-144, See FIG. 3B).

Example 2

MMP9 Proteolytic Activity Measured Using Gelatin Zymography

THP-1 cells were incubated with TNF-α and IL-6. After incubation for 24 hours, conditioned media were collected and mixed with Zymogram sample buffer (BioRad; 62.5 mM Tris-HCl, pH.6.8, 25% glycerol, 4% SDS and 0.01% bromophenol blue) and then loaded on to a 10% polyacrylamide gel with gelatin (10% Ready Gel Zymogram Gel, BioRad) for electrophoresis. The gel was incubated with renaturing buffer BioRad (2.5% Triton X-100) for 1 hour at room temperature and Incubated with zonogram developing buffer. BioRad (50 mM Tris-HCl, pH 7.5, 200 mM NaCl and 5 mM $CaCl_2$ for 24 hours at 37° C. Gels were stained with slanting solution (0.5% Coomassie Brilliant Blue R-250 (BioRad, Hercules, Calif.), 40% Methanol, 10% Acetic Acid) for 2 hours and then destained with destaining solution (40% Methanol, 10% Acetic Acid) until the bunds appeared. Proteolytic activity was indicated as clear bands against the black background of stained gel. As Illustrated in FIG. 2, the strongest proteolytic activity of MMP-9 was observed when monocytes were stimulated by TNF-α and IL-6, lesser MMP-9 proteolytic activity was observed when monocytes were stimulated by TNF-α alone, and minimal MMP-9 proteolytic activity was observed when monocytes were stimulated by IL-6 alone. These results further support the conclusion that there is a crosstalk between the TNF-α and IL-6 signaling pathways that results in a significant increase in MMP-9 expression, secretion, and proteolytic activity.

It is to be understood that the system and method for doing something is not limited to the specific embodiments described above, but encompasses any and alt embodiments within the scope of the generic language of the following claims enabled by the embodiments described herein, or otherwise shown m the drawings or described above in terms sufficient to enable one of ordinary skill in the art to make and use the claimed subject matter.

We claim:

1. A method for inhibiting MMP-9 expression or secretion, comprising administering an IL-6 inhibitor to a subject in need thereof; wherein the IL-6 inhibitor inhibits crosstalk between IL-6 and TNF-α; and wherein the IL-6 inhibitor is selected from the group consisting of AG490, SC-144, and a combination thereof.

2. The method of claim 1, wherein the IL-6 inhibitor inhibits IL-6 and TNF-α mediated promotion of MMP-9 mRNA expression.

3. The method of claim 1, wherein the IL-6 inhibitor inhibits IL-6 and TNF-α mediated promotion of MMP-9 protein expression.

4. A method of preventing progression of a cardiovascular disease or a cancer comprising administering an effective amount of an IL-6 inhibitor sufficient to reduce MMP-9 expression or secretion to a subject in need thereof; wherein the IL-6 inhibitor inhibits crosstalk between IL-6 and TNF-α; and wherein the IL-6 inhibitor is selected from the group consisting of AG490, SC-144, and a combination thereof.

5. The method of claim 4, wherein the IL-6 inhibitor inhibits IL-6 and TNF-α mediated promotion of MMP-9 mRNA expression.

6. The method of claim 4, wherein the IL-6 inhibitor inhibits IL-6 and TNF-α mediated promotion of MMP-9 protein expression.

7. The method of claim 4, wherein the disease is cancer and the method further comprises providing at least one therapeutic benefit selected from the group consisting of inhibition of the formation of metastasis, inhibition of tumor progression, inhibition of invasion, and inhibition of tumor growth.

* * * * *